(12) United States Patent
Seed et al.

(10) Patent No.: US 6,596,703 B1
(45) Date of Patent: Jul. 22, 2003

(54) PROMOTION OF WOUND HEALING UTILIZING STEROIDS HAVING REDUCED DETERIOROUS SYSTEMIC SIDE EFFECTS TYPICAL OF GLUCOCORTICOIDS, MINERALOCORTICOIDS AND SEX STEROIDS

(75) Inventors: Michael P. Seed; Chandan Alam; Derek A. Willoughby, all of London (GB)

(73) Assignee: Jagotec AG, Hergisweil (CH)

( * ) Notice: Subject to any disclaimer, the term of this patent is extended or adjusted under 35 U.S.C. 154(b) by 0 days.

(21) Appl. No.: 08/893,620

(22) Filed: Jul. 11, 1997

(51) Int. Cl.[7] ............................................. A61K 31/70
(52) U.S. Cl. ........................................ 514/54; 514/171
(58) Field of Search ............................ 519/171; 579/54

(56) References Cited

U.S. PATENT DOCUMENTS

| | | | |
|---|---|---|---|
| 4,771,042 A | 9/1988 | Braughler et al. | 514/171 |
| 4,975,537 A | 12/1990 | Aristoff et al. | 540/9 |
| 5,336,767 A | 8/1994 | della Valle et al. | 536/55.1 |
| 5,506,354 A | 4/1996 | McCall et al. | 540/5 |
| 5,798,334 A * | 8/1998 | Cutroneo | 574/12 |
| 5,820,874 A * | 10/1998 | Maloney et al. | 424/443 |

FOREIGN PATENT DOCUMENTS

| | | | |
|---|---|---|---|
| EP | 0 221 705 | 5/1987 | C07J/5/00 |
| WO | WO 87/02672 | 5/1987 | C07J/5/00 |
| WO | WO 90/12577 | 11/1990 | A61K/31/51 |
| WO | WO 90/15816 | 12/1990 | C07J/3/00 |
| WO | WO 91/19731 | 12/1991 | C07J/31/00 |
| WO | WO 94/17840 | 8/1994 | A61K/31/725 |
| WO | WO 94/23725 | 10/1994 | A61K/31/725 |

OTHER PUBLICATIONS

Opal Ka, C.J. et al., *Synthesis* (1995): 766–8.
Cockerill, G.W. et al., *International Review of Cytology* (1995) 159: 113–60.
Diaz–Flores, L. et al., *Histology and Histopathology* (Oct. 1994) 9(4): 807–43.
Sipos, E.P. et al, *Annals of the New York Academy of Sciences* (Sep. 6, 1994); 732: 263–72.
Thorpe, P.E. et al., *Cancer Research* (Jul. 1, 1993) 53(13): 3007–7.
Folkman, J. and Ingber, D., *Seminars in Cancer Biology* (Apr. 1992) 3(2): 89–96.
Ribatti, D. et al., *Haematologica* (Jul.–Aug. 1991) 76(4): 311–20.
Tobelem, G., *Blood Coagulation and Fibrinolysis* (Dec. 1990) 1(6): 703–5.
Wilks, J.W. et al., *International Journal of Radiation Biology*, (Jul.–Aug. 1991) 60(1–2): 73–7.
Folkman, J. et al., *Science* (Mar. 17, 1989) 243(4897): 1490–3.
Cariou, R. et al., *Cell Biology International Reports* (Dec. 1988) 12(12): 1037–47.
Folkman, J. and Ingber, D.E., *Annals of Surgery* (Sep. 1987) 206(3): 374–83.
Ingber, D.E. et al, *Endocrinology* (Oct. 1986) 119(4): 1768–75.
Folkman, J. *Cancer Research* (Feb. 1986) 46(2): 467–73.
Crum, R. et al., *Science* (Dec. 20, 1985) 230(4732): 1375–8.
Folkman, J., *Pediatrics* (Nov. 1984) 74(5): 850–6.
Blei, F. et al., *Journal of Cellular Physiology* (Jun. 1993) 155(3): 568–78.
Folkman, J. and Shing Y., *Advances in Experimental Medicine and Biology* (1992) 313:555–64.
Yamamoto, T., Terada, N., Nishizawa, Y. and Petrow, V., *Angiostatic Activities of Medroxyprogesterone Acetate and its Analogues* (1994): 56, 393–399.
Colville–Nash, P., Alam, C., Appleton, I., Brown, J., Seed, M. and Willoughby, D., *The Pharmacological Modulation of Angiogenesis in Chronic Granulomatous Inflammation* (1995) JPET 274: 1463–1472.

* cited by examiner

*Primary Examiner*—Elli Peselev
(74) *Attorney, Agent, or Firm*—Leydig, Voit & Mayer, Ltd.

(57) ABSTRACT

A pharmaceutical composition utilized for increasing neovascularization and angiogenesis during wound healing in a mammal beyond the level of neovascularization and angiogenesis which would occur at the wound site without any treatment, said composition comprising an effective amount of any angiostatic steroid which has reduced or no deteriorative or detrimental side effects combined with an effective amount of a form of hyaluronan such as hyaluronic acid and pharmaceutically acceptable salts thereof.

38 Claims, 3 Drawing Sheets

PROMOTION OF WOUND HEALING UTILIZING STEROIDS HAVING REDUCED DETERIOROUS SYSTEMIC SIDE EFFECTS TYPICAL OF GLUCOCORTICOIDS, MINERALOCORTICOIDS AND SEX STEROIDS

FIELD OF INVENTION

This invention relates to the use of angiostatic steroids, which are known to have reduced or no systemic side effects typical of glucocorticoids, mineralocorticoids and sex steroids, for the promotion of angiogenesis and thus wound healing when used in combination with hyaluronan (for example hyaluronan and pharmaceutically acceptable salts thereof). This invention in one particular application may be used in creams, lotions, sprays, suppositories, and gels and the like for application in wound healing for delivery of for example an effective amount of tetrahydro steroids in combination with an effective amount of hyaluronic acid to the wound site, for example to treat incisions, burns, skin lesions, and ulcers. Equally appropriate applications would be administration of the invention intradermally, transdermally, intermuscularly, intramuscularly and intravenously when appropriate.

It is well documented that tetrahydro steroids such as tetrahydrocortisol (TH-F), tetrahydrocortisone (TH-E) and tetrahydrocortexolone (TH-S) are known not to possess the detrimental systemic side effects normally associated with glucocorticoids, mineralocorticoids and sex steroids since they do not bind to appropriate receptors such as do known glucocorticoids, mineralocorticoids and sex steroids. Typically, the continued use of glucocorticoids, mineralocorticoids and sex steroids for chronic ailments may result in a number of well known documented side effects such as bone wasting, fluid retention and infections. Therefore, these glucocorticoid steroids, mineralocorticoids and sex steroids are normally not recommended for a chronic program of treatment for patients. Thus for wound healing for chronic type wounds such as dermatitis, skin ulcers, hemorrhoids, and the like although they would benefit from the use of these aforementioned steroids, the expected systemic side effects would materialize.

The tetrahydra steroids are themselves angiostatic steroids. Other steroids are also angiostatic or anti-angiogenic steroids. They are known not to possess detrimental systemic side effects normally associated with glucocorticoids, mineralocorticoids and sex steroids. These angiostatic steroids have therefore very much reduced detrimental side effects (and in some instances are known not to possess these side effects). These angiostatic steroids are also normally associated with the inhibition of new blood vessel formation. For a discussion of the various research and use of angiostatic steroids, the reader is referred to the following listing of patents, patent applications and technical articles which are representative only and are not in any way implied to be an exhaustive listing. Throughout this disclosure, "angiostatic steroids" or the like are to be assumed to mean those steroids not possessing significant angiogenetic properties.

| Country | Patent No. | Title of Invention | Inventors | Assignee |
|---|---|---|---|---|
| US | 4,771,042 | Inhibition of Angiogenesis Involving the Coadministration of Steroids with Heparin or Heparin Fragments | John M. Braughler; Edward D. Hall, both of Portage; John M. McCall, Kalamazoo; Wendell Wierenga, Oshtemo Township, Kalamazoo County, Mich.; Judah Folkman, Brookline, Mass. | The Upjohn Company, Kalamazoo, Mich. |
| US | 4,975,537 | Angiostatic Steroids | Paul A. Aristoff, Portage; Harvey I. Skulnick; Wendell Wierenga, both of Kalamazoo, all of Mich. | The Upjohn Company, Kalamazoo, Mich. |
| US | 5,336,767 | Total or Partial Esters of Hyaluronic Acid | Francesco della Valle, Padova; Aurelio Romeo, Rome, both of Italy | Fidia, S.p.A., Abano Terme, Italy |
| US | 5,506,354 | Imidazolyl-piperazinyl Steroids | John M. McCall; Donald E. Ayer, both of Kalamazoo; E. Jon Jacobsen, Plainwell; Frederick J. VanDoornik, Hamilton; John R. Palmer; Harold A. Karnes, both of Kalamazoo, all of Mich. | The Upjohn Company, Kalamazoo, Mich. |
| PCT | WO 87/02672 | Tetrahydro Angiostatic Steroids | Paul Aristoff, Harvey I. Skulnick, Wendell Wierenga | The Upjohn Company |
| PCT | WO 90/12577 | Topical Anti-Angiogenic as Hair Growth Inhibitors | J. Holland, Duane B. Lakings | The Upjohn Company |
| PCT | WO 90/15816 | Suramin Type Compounds and Angiostatic Steroids to Inhibit Angiogenesis | Paul A. Aristoff, Mark A. Mitchell, John W. Wilks | The Upjohn Company |
| PCT | WO 91/19731 | Steroids which Inhibit Angiogenesis | John Wilks, Thomas Frank Dekoning, Paul Adrian Aristoff | The Upjohn Company |
| PCT | WO 94/17840 | Pharmaceutical Compositions Comprising a Spongy Material Consisting of Ester Derivatives of Hyaluronic Acid Combined with Other Pharmacologically Active Substances | Alberto Perbellini, Riccardo Gabriele Ferretti, Franco Dorigatti, Lanfranco Callegro | |
| EP | 0 221 705 | Tetrahydro Angiostatic Steroids | Paul A. Aristoff, Harvey I. Skulnick, Wendell Wierenga | The Upjohn Company |

Journal Articles

1. Opal Ka, C. J. et al., *Synthesis* (1995): 766–8.
2. Cockerill, G. W. et al., *International Review of Cytology* (1995) 159: 113–60.
3. Diaz-Flores, L. et al.,*Histology and Histopathology* (October 1994) 9(4): 807–43.

4. Sipos, E. P. et al, *Annals of the New York Academy of Sciences* (Sep. 6, 1994); 732: 263–72.
5. Thorpe, P. E. et al., *Cancer Research* (Jul. 1, 1993) 53(13): 3000–7.
6. Folkman, J. and Ingber, D., *Seminars in Cancer Biology* (April 1992) 3(2): 89–96.
7. Ribatti, D. et al., *Haematologica* (July–August 1991) 76(4): 311–20.
8. Tobelem, G., *Blood Coagulation and Fibrinolysis* (December 1990) 1(6): 703–5.
9. Wilks, J. W. et al., *International Journal of Radiation Biology*, (July–August 1991) 60(1–2): 73–7.
10. Folkman, J. et al., *Science* (Mar. 17, 1989) 243(4897): 1490–3.
11. Cariou, R. et al., *Cell Biology International Reports* (December 1988) 12(12): 1037–47.
12. Folkman, J. and Ingber, D. E., *Annals of Surgery* (September 1987) 206(3): 374–83.
13. Ingber, D. E. et al, *Endocrinology* (October 1986) 119(4): 1768–75.
14. Folkman, J., *Cancer Research* (February 1986) 46(2): 467–73.
15. Crum, R. et al., *Science* (Dec. 20, 1985) 230(4732): 1375–8.
16. Folkman, J., *Pediatrics* (November 1984) 74(5): 850–6.
17. Blei, F. et al., *Journal of Cellular Physiology* (June 1993) 155(3): 568–78.
18. Folkman, J. and Shing Y., *Advances in Experimental Medicine and Biology* (1992) 313: 355–64.
19. Yamamoto, T., Terada, N., Nishizawa, Y. and Petrow, V., *Angiostatic Activities of Medroxyprogesterone Acetate and its Analogues* (1994): 56, 393–399.
20. Colville-Nash, P., Alam, C., Appleton, I., Brown, J., Seed, M. and Willoughby, D., *The Pharmacological Modulation of Angiogenesis in Chronic Granulomatous Inflammation* (1995) JPET 274: 1463–1472. Since wound healing depends on angiogenesis, (the reader is directed to article 3 above at page 811 for a discussion of angiogenesis) it would be desirable to induce angiogenesis utilizing safe compounds and which compounds do not have systemic side effects typical of glucocorticoids, mineralocorticoids and sex steroids, or at least substantially reduced side effects. However, the angiostatic steroids have not previously been recognized to stimulate new blood vessel growth. See for example, article 4 and page 265 therein. Specific reference is made to article 19 above to Nishizawa which verifies that angiostatic steroids do not bind glucocorticoid, mineralocorticoid and sex steroid receptors.

Applicants have in their PCT Application WO94/23725 published on Oct. 27, 1994 by Professor Willoughby et al., utilized an NSAID in combination with a form of hyaluronic acid for controlling, inhibiting, and/or regressing angiogenesis for the treatment of tumours and other diseases and conditions.

PCT Application WO94/17840 to Fidia published Aug. 18, 1994 discusses a spongy material consisting of total or partial ester derivatives of hyaluronic acid utilized for the administration of hyaluronic acid solutions to enhance the recovery of patients suffering from decubitus ulcers, wounds and burns. This document purports to describe the capability of hyaluronic acid to induce a rapid and complete tissue repair process. It is discussed further that anti-inflammatory agents may be contained in the solutions of hyaluronic acid. Specifically, the reference purports to teach a combination of hyaluronic acid in solution with, for example, corticosteroids which include glucocorticoids and mineralocorticoids. These steroids are known to have undesirable systemic side effects.

It is therefore an object of this invention to provide a novel treatment for promoting the formation of blood vessel growth and proliferation (angiogenesis) for wound healing.

It would also be advantageous to be able to utilize substantially reduced levels of medicines for wound healing in relation to the levels normally required when the treatment involves the use of corticosteroids. Typically when corticosteroids are used for a topical treatment, formulations 0.1 to 1% incorporating corticosteroids are used. It would also be advantageous if corticosteroids are used to reduce the amount used. Furthermore, it is an object of this invention to utilize other compounds heretofore not known for promotion of angiogenesis to stimulate angiogenesis.

Further and other objects of the invention will become apparent to those skilled in the art from the following summary of the invention and the more detailed description of embodiments thereof.

SUMMARY OF THE INVENTION

According to one aspect of this invention, we have provided compositions including known steroids such as angiostatic steroids which have limited or no angiogenic effect in combination with a form of hyaluronic acid which in combination results in accelerated scarless wound healing and the stimulation of new blood vessel formation (angiogenesis).

According to another aspect of the invention, angiogenesis is promoted in wound healing treatment by, for example topical application, by utilizing significantly lower dosages of agents such as angiostatic anti-inflammatory agents such as known angiostatic steroids having significantly reduced or no systemic side effects, (when compared to glucocorticoids, mineralocorticoids and sex steroids), in combination with a form of hyaluronic acid to foster and induce angiogenesis when utilized in combination with the form of hyaluronic acid in wound healing and for the stimulation of new blood vessels in the acceleration of scarless wound healing.

According to another aspect of the invention, the compositions and treatment include steroids known not to possess detrimental systemic side effects typical of glucocorticoid, mineralocorticoid and sex steroids in combination with a form of hyaluronic acid (such as hyaluronan and pharmaceutically acceptable salts thereof) for topical application for wound healing and which combination induces angiogenesis and accelerates scarless wound healing.

Therefore, according to another aspect of the invention there is provided a pharmaceutical composition utilized for increasing neovascularization and angiogenesis during wound healing in a mammal, for example a human, beyond the level of neovascularization and angiogenesis which would occur at the wound site without any treatment, said composition comprising an effective amount of any angiostatic steroid combined with an effective amount of a form of hyaluronan such as hyaluronic acid and pharmaceutically acceptable salts thereof. Preferably, said composition includes a suitable diluent such as purified water or the like. The composition may be applied or administered nasally, vaginally, intraaurally, ocularily, rectally, orally, locally or topically at preferred levels of 0.1–3mg of said steroid per kg of body weight of the patient preferably within the order of about 2.5% hyaluronic acid by weight in the formulation. In various embodiments, 0.1–20% hyaluronic acid by weight of the formulation may be utilized and preferably 0.3–10% may be utilized. Suitable compositions may also be formulated for application of the compositions of the invention transdermally, intermuscularly, intramuscularly and intravenously when appropriate.

According to yet another aspect of the invention there is provided a method of treatment for increasing neovascularization and angiogenesis during wound healing in a mammal, for example a human, beyond the level of neovascularization and angiogenesis which would occur at the wound site without any treatment, said method comprising application of a composition including an effective amount of any angiostatic steroid combined with an effective amount of a form of hyaluronic acid (such as hyaluronan and pharmaceutically acceptable slats thereof) at the wound site. Preferably said composition includes a suitable diluent such as purified water or the like. The composition may be applied or administered nasally, vaginally, intraaurally, ocularly, rectally, orally, locally or topically at preferred levels of 0.1–3mg of the steroid per kilogram of body weight of the patient in a composition comprising in the order of about preferably 2.5% hyaluronic acid by weight. Alternatively, formulations containing 0.1–20% hyaluronic acid by weight may be utilized and preferably 0.3–10% may be utilized together with an angiostatic steroid which is in the order of 0.1–1 mg of the steroid per kilogram of body weight. Suitable compositions can be formulated for administration transdermally, intermuscularly, intramuscularly and intravenously when appropriate.

According to yet another aspect of the invention there is provided the use of a pharmaceutical composition for increasing neovascularization and angiogenesis during wound healing in a mammal beyond the level of neovascularization and angiogenesis which would occur at the wound sight without any treatment, said use of said composition comprising application of the composition containing an effective amount of an angiostatic steroid combined with an effective amount of a form of hyaluronan such as hyaluronic acid and a pharmaceutically acceptable salt thereof at the wound site. Preferably said composition also includes a suitable diluent such as purified water or the like. The composition may be applied or administered nasally, vaginally, intraaurally, ocularly, rectally, orally, locally or topically at preferred levels of 0.1–3 mg of said steroid per kg of body weight of the patient with for example 2.5% hyaluronic acid by weight of the composition. Alternatively 0.1–20% hyaluronic acid may be utilized by weight in the formulation, and more preferably 0.3–10% by weight of the composition may be a form of hyaluronic acid. Equally appropriate would be the application of the invention transdermally, intermuscularly, intramuscularly and intravenously when appropriate.

According to yet another aspect of the invention, there is provided a composition for inducing angiogenesis in the healing of a condition, such as a wound, for example for topical application, said composition comprising a form of hyaluronic acid in a suitable form and effective amount in combination with an effective amount of a suitable steroid, such as angiostatic steroids, for example tetrahydro-steroids, that are known not to possess detrimental systemic side effects or to possess significantly reduced detrimental side effects such as bone mass loss, fluid retention, infections and the like as is normally associated with glucocorticoids, mineralocorticoids, and sex steroids, said suitable steroid, such as an angiostatic steroid, (for example tetrahydro-steroids known not to stimulate new blood vessel formation when utilized individually) wherein the combination of hyaluronic acid and said suitable steroid (known to possess reduced detrimental side effects, or not to possess detrimental systemic side effects, normally associated with glucocorticoids, mineralocorticoids and sex steroids and which are normally angiostatic and inhibit new blood vessel formation), stimulates new blood vessel formation and angiogenesis to accelerate scarless healing of a condition such as a wound. Preferably, the steroids such as tetrahydrocortisol (THF), tetrahydrocortisone (THE) and tetrahydrocortexolone (THS) known not to possess detrimental systemic side effects and known to be angiostatic are the agents combined with the form of hyaluronic acid. The reader is referred to the previous prior art listing for a partial listing of typical angiostatic steroids. For example, a combination of the form of hyaluronic acid in combination with tetrahydro-steroid derivatives would be beneficial for acceleration of wound healing by the stimulation of angiogenesis.

According to another aspect of the invention, there is provided a process for the stimulation and/or induction of angiogenesis, for example, stimulation of blood vessel growth in a condition such as a wound in a mammal (for example a human), the process comprising the step of administering an effective dosage amount of a pharmaceutical composition for the stimulation and/or induction of angiogenesis to a site on/in a mammal in need of stimulation and/or induction of angiogenesis such as at a wound site, and repeating the administration for such time as required, each effective dosage amount of the composition comprising an effective non-toxic dosage amount of a steroid known to have angiostatic properties when utilized alone or in combination with known therapies, examples of which angiostatic steroids include tetrahydro-steroids, for example tetrahydrocortisone, tetrahydrocortisol or tetrahydrocortexolone or the like (for example, in solution in the composition), and an effective non-toxic dosage amount of a form of hyaluronic acid and/or a pharmaceutically acceptable salt thereof (for example, sodium hyaluronate) preferably sodium hyaluronate. Preferably, the composition may be administered topically in the form of a cream, lotion and/or gel for the treatment of burns, ulcers, incisions or the like, nasally, vaginally, intraurally, ocularly, or orally for the treatment of wounds therein or as a suppository for hemorrhoids. Administration may also comprise application transdermally, intermuscularly, intramuscularly and intravenously when appropriate.

According to another aspect of the invention, the use of a combination of a form of hyaluronic acid (for example, hyaluronic acid and a pharmaceutically acceptable salt thereof) for example, sodium hyaluronate, and a suitable steroid known not to have systemic side effects, such as angiostatic steroids, for example tetrahydro-steroids such as tetrahydrocortisol, tetrahydrocortisone or tetrahydrocortexolone and the like (among others also known not to have the systemic side effects of glucocorticoids, mineralocorticoids and sex steroids or the like,) which are also known to be normally angiostatic when administered in known compositions or solutions is provided for angiogenesis. Surprisingly and unexpectedly, this combination of the form of hyaluronic acid with the specified agent stimulates and induces angiogenesis and hence healing of a condition such as a wound. The composition may be applied or administered nasally, vaginally, intraaurally, ocularly, rectally, orally, locally or topically at preferred levels of 0.1–3 mg of said steroid per kilogram of the patient in combination with 0.1–20% by weight of the form of hyaluronic acid in the composition, preferably 0.3–10% by weight of the form of hyaluronic acid may be used in the formulation. Equally appropriate would be the application of the compositions transdermally, intermuscularly, intramuscularly and intravenously when appropriate.

Thus, an effective non-toxic dosage amount of a composition comprising an effective non-toxic dosage amount of sodium hyaluronate and a therapeutically effective non-toxic dosage amount of a known angiostatic steroid, such as tetrahydro-steroids for example tetrahydrocortisol, tetrahydrocortisone or tetrahydrocortexolone or the like is provided and may be used to stimulate and induce angiogenesis. The amount of angiostatic steroid (for example, tetrahydrocortisol, tetrahydrocortisone or tetrahydrocortexolone or the like) administered in one example may be about 0.1–3 mg/kg of body weight of the patient for application topically in a composition which comprises preferably 2.5% hyaluronic acid or salt thereof by weight for wounds in the order of 4 sq. cm. Alternatively, the composition may comprise about 0.1–20% hyaluronic acid, preferably 0.3–10% by weight of the composition may be utilized.

According to another aspect of the invention, a pharmaceutical composition (suitable for, topical application [on the skin], rectally, vaginally, intraaurally, ocularly, locally, nasally, orally, on the mucosa, etc.) is provided (for example a multigram pharmaceutical composition for use topically) effective for the stimulation and induction of angiogenesis, the pharmaceutical composition containing a plurality of dosage amounts for stimulating and inducing angiogenesis, each of said dosage amounts comprising a therapeutically effective non-toxic (to the patient) dosage amount of a steroid known to be angiostatic (for example tetrahydrosteroids) as described above and in the literature and an effective non-toxic dosage amount of the form of hyaluronic acid such as hyaluronan and/or pharmaceutically acceptable salts thereof effective to stimulate and induce angiogenesis. Equally appropriate would be the application of the composition transdermally, intermuscularly and intramuscularly when appropriate.

The pharmaceutical composition may comprise suitable excipients depending upon the route of administration for example excipients to make a gel, lotion, spray, ointment, suppository, or cream (topical administration).

According to yet another aspect of the invention, a dosage amount of a pharmaceutical composition is provided for stimulating and inducing angiogenesis at a wound site, the composition comprising:
(1) a known angiostatic steroid agent known not to have systemic side effects typical of glucocorticoids, mineralocorticoids and sex steroids, for example tetrahydrosteroids; and
(2) a form of hyaluronic acid and/or pharmaceutically acceptable salts thereof (for example sodium hyaluronate) characterized in that said composition:
 (a) is in a dosage form (e.g. in a cream, lotion, gel, ointment, spray, or solution, etc.) which is suitable for administration at the wound site; and
 (b) is in such an amount and in such form that component (1) is in an effective dosage amount together with component (2) to stimulate and induce angiogenesis (for example in scarless wound healing). Preferably, the pharmaceutical composition may further comprise a plurality of dosage amounts.

According to still another aspect of the invention there is provided the use of
(1) a known angiostatic steroid agent known not to have systemic side effects typical of glucocorticoids, mineralocorticoids and sex steroids, for example tetrahydrosteroids; and
(2) hyaluronic acid and/or pharmaceutically acceptable salts thereof (for example sodium hyaluronate) in the manufacture of a pharmaceutical composition for use to stimulate and induce angiogenesis in mammals (for example in humans) at a wound site, wherein dosage amounts may be taken from the composition and each dosage amount taken comprises:
 a therapeutically effective non-toxic dosage amount of each of components (1) and (2) to stimulate and induce angiogenesis at said wound site.

The composition containing the form of hyaluronic acid and known angiostatic steroid provides significantly greater stimulation of angiogenesis than a composition comprising a form of hyaluronic acid (for example sodium hyaluronate) only. Thus, according to another aspect of the invention Applicants have provided similar methods of treatment, pharmaceutical compositions, dosage amounts and uses comprising forms of hyaluronic acid (for example sodium hyaluronate having a molecular weight less than about 750,000 daltons) with the angiostatic steroids known not to have systemic side effects typical of glucocorticoids, mineralocorticoids and sex steroids.

The amount of the form of hyaluronic acid (for example sodium hyaluronate) per dosage amount may vary. A concentration of 0.1–20% hyaluronic acid may be utilized in the composition by weight and preferably 0.3%–10% may be utilized. Preferably the form of hyaluronic acid (for example sodium hyaluronate) administered, has a molecular weight less than about 750,00 daltons (for example about 150,00 to about 225,000 daltons). While higher molecular weights of the hyaluronic acid and forms thereof may be used in the compositions to stimulate angiogenesis, where the molecular weight of the hyaluronic acid chosen for use is very large, the form of hyaluronic acid is autoclaved, to break down the form of hyaluronic acid to fragments of lesser molecular weight and if feasible diluted to permit administration and ensure no coagulation (whatever the route of administration). Where the molecular weight of the form of hyaluronic acid being employed is at the upper range, the concentration of the form of the hyaluronic acid in the composition may be adjusted, for example be reduced (for example to less than about 1%) dependent on the molecular weight.

Many forms of hyaluronan may be suitable although those preferred are those discussed hereinafter (identified Molecular Weights were determined using the Protein Standard):

One form of hyaluronic acid and/or pharmaceutically acceptable salts thereof (for example sodium salt) suitable for use with our invention is an amount having the following specifications/characteristics:

| TESTS | SPECIFICATIONS | RESULTS |
| --- | --- | --- |
| pH | 5.0 to 7.0 at 25 degrees C. | 6.0 |
| Specific Gravity | 0.990 to 1.010 at 25 degrees C. | 1.004 |
| Intrinsic Viscosity | 4.5 to 11.0 dL/g. | 7.07 |
| Molecular Weight | 178,000 to 562,000 daltons | (protein 319,378 daltons standard) |
| Sodium Hyaluronate Assay and Identification | 9.0 to 11.0 mg/mL. Positive | 9.9 mg/ML Positive |

Another such amount may comprise:

| TESTS | SPECIFICATIONS |
|---|---|
| 1. Description | White or cream odourless powder |
| 2. Identification (IR Spectrum) | Conforms to Ref. Std. Spectrum |
| 3. pH (1% solution) | 5.0 to 7.0 |
| 4. Loss on Drying | NMT 10% |
| 5. Residue on Ignition | 15.0% to 19.0% |
| 6. Protein Content | NMT 0.1% |
| 7. Heavy Metals | NMT 20 ppm |
| 8. Arsenic | NMT 2 ppm |
| 9. Residual Solvents | |
| a) Formaldehyde | NMT 100 ppm |
| b) Acetone | NMT 0.1% |
| c) Ethanol | NMT 2.0% |
| 10. Sodium Hyaluronate Assay (dried basis) | 97.0 to 102.0% |
| 11. Intrinsic Viscosity | 10.0 to 14.5 dL/g |
| 12. Molecular Weight | 500,000 to 800,000 daltons |
| 13. Total Aerobic Microbial Count (USP 23) | NMT 50 microorganisms/g |
| 14. *Escherichia coli* (USP 23) | Absent |
| 15. Yeasts and Moulds (USP 23) | NMT 50 microorganisms/g |
| 16. Bacterial Endotoxins (LAL) (USP 23) | NMT 0.07 EU/mg |

Another such amount is available from Hyal Pharmaceuticals Limited and comes in a 15 ml vial of Sodium hyaluronate 20 mg/ml (300 mg/vial-Lot 2F3). The sodium hyaluronate amount is a 2% solution with a mean average molecular weight of about 225,000. The amount also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The amount of hyaluronic acid and/or salts thereof (for example sodium salt) may also comprise the following characteristics:

a purified, substantially pyrogen-free amount of hyaluronic acid obtained from a natural source having at least one characteristic selected from the group (and preferably all characteristics) consisting of the following:
  i) a molecular weight within the range of 150,000–225,000;
  ii) less than about 1.25% sulphated mucopolysaccharides on a total weight basis;
  iii) less than about 0.6% protein on a total weight basis;
  iv) less than about 150 ppm iron on a total weight basis;
  v) less than about 15 ppm lead on a total weight basis;
  vi) less than 0.0025% glucosamine;
  vii) less than 0.025% glucuronic acid;
  viii) less than 0.025% N-acetylglucosamine;
  ix) less than 0.0025% amino acids;
  x) a UV extinction coefficient at 257 nm of less than about 0.275;
  xi) a UV extinction coefficient at 280 nm of less than about 0.25; and
  xii) a pH within the range of 7.3–7.9. Preferably, the hyaluronic acid is mixed with sterile water and the amount of hyaluronic acid has a mean average molecular weight within the range of 150,000–225,000 daltons (protein standard). More preferably, the amount of hyaluronic acid comprises at least one characteristic selected from the group (and preferably all characteristics) consisting of the following characteristics:
  i) less than about 1% sulphated mucopolysaccharides on a total weight basis;
  ii) less than about 0.4% protein on a total weight basis;
  iii) less than about 100 ppm iron on a total weight basis;
  iv) less than about 10 ppm lead on a total weight basis;
  v) less than 0.00166% glucosamine;
  vi) less than 0.0166% glucuronic acid;
  vii) less than 0.0166% N-acetylglucosamine;
  viii) less than 0.00166% amino acids;
  x) a UV extinction coefficient at 257 nm of less than about 0.23;
  xi) a UV extinction coefficient at 280 nm of less than 0.19; and
  xii) a pH within the range of 7.5–7.7

Applicants may also use sodium hyaluronate produced and supplied by LifeCore™ Biomedical, Inc., having the following specifications:

| Characteristics | Specification | | | | | | | |
|---|---|---|---|---|---|---|---|---|
| Appearance | White to cream colored particles | | | | | | | |
| Odor | No perceptible odor | | | | | | | |
| Viscosity Average Molecular Weight | <750,000 Daltons | | | | | | | |
| UV/Vis Scan, 190–820 nm | Matches reference scan | | | | | | | |
| OD, 260 nm | <0.25 OD units | | | | | | | |
| Hyaluronidase Sensitivity | Positive response | | | | | | | |
| IR Scan | Matches reference | | | | | | | |
| pH, 10 mg/g solution | 6.2–7.8 | | | | | | | |
| Water | 8% maximum | | | | | | | |
| Protein | <0.3 mcg/mg NaHy | | | | | | | |
| Acetate | <10.0 mcg/mg NaHy | | | | | | | |
| Heavy Metals, maximum ppm | | | | | | | | |
| As | Cd | Cr | Co | Cu | Fe | Pb | Hg | Ni |
| 2.0 | 5.0 | 5.0 | 10.0 | 10.0 | 25.0 | 10.0 | 10.0 | 5.0 |
| Microbial Bioburden | None observed | | | | | | | |
| Endotoxin | <0.07 EU/mg NaHy | | | | | | | |
| Biological Safety Testing | Passes Rabbit Ocular Toxicity Test | | | | | | | |

Another amount of sodium hyaluronate proposed to be used is sold under the name Hyaluronan HA-M5070 by Skymart Enterprises, Inc. having the following specifications:

| Specifications Test Results | |
|---|---|
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW:679,000) |
| Nitrogen | 3.14% |
| Assay | 104.1% |
| Microbiological Counts | 80/g |
| *E. coli* | Negative |
| Mold and Yeast | Not more than 50/g |

Other forms of hyaluronic acid and/or its salts may be chosen from other suppliers and those described in prior art documents provided they are suitable.

The following references teach hyaluronic acid, sources thereof, and processes for the manufacture and recovery thereof which may be suitable.

As there is no toxicity of the form of hyaluronic acid, the form of hyaluronic acid may be administered in doses in excess of 12 mg/kg of body weight, for example, in excess of 1000 mg/70 kg person and even up to amounts of 3000 mg/70 kg person without adverse toxic effects. Lower amounts may include 10–50 mg of hyaluronan. Example amounts of Hyaluronan used may be 3–10mg of HA/kg of body weight of the patient wherein the molecular weight (protein standard) is less than 750,000 daltons.

Suitable forms of hyaluronan may have molecular weights of forms of hyaluronan between about 150,000 daltons and about 750,000 daltons (protein standard) in sterile water prepared having a viscosity for intravenous administration.

One specific form of pharmaceutical grade is a 1% sterile sodium hyaluronate solution (50 ml vials) provided by Hyal Pharmaceutical Corporation which has the following characteristics:

| | Tests | Specifications |
|---|---|---|
| 1. | Container Description | 150 mL Flint glass vial with a red or gray rubber stopper and an aluminum seal, 20 mm in size. |
| 2. | Product Description | A clear, colourless, odourless, transparent, slightly viscous liquid. |
| 3. | Fill Volume | 50.0 to 52.0 mL |
| 4. | pH | 5.0 to 7.0 at 25 degrees C. |
| 5. | Specific Gravity | 0.990 to 1.010 at 25 degrees C. |
| 6. | Intrinsic Viscosity | 4.5 to 11.0 dL/g |
| 7. | Molecular Weight | 178,000 to 562,000 daltons |
| 8. | Sodium Hyaluronate Assay and Identification | 9.0 to 11.0 mg/mL. Positive |
| 9. | Particulate Matter | No visible Particulate Matter |
| 10. | Sterility | Meets Requirements for Sterility, USP 23 |
| 11. | Bacterial Endotoxins (LAL) | Meets Requirements for Bacterial Endotoxins, USP 23. |

This pharmaceutical grade 1% sterile solution of hyaluronan may be made from granules/powder having the following characteristics:

| | Tests | Specifications |
|---|---|---|
| 1. | Description | White or cream-coloured granules or powder, odourless |
| 2. | Identification (IR Spectrum) | Must conform with the Reference Standard Spectrum. |
| 3. | pH (1% Solution) | Between 5.0 and 7.0 at 25 degrees C. |
| 4. | Loss on Drying | NMT 10.0% at 102 degrees C. for 6 hours. |
| 5. | Residue on Ignition | Between 15.0 and 19.0% |
| 6. | Protein Content | NMT 0.10% |
| 7. | Heavy Metals | NMT 20 ppm (as per USP 23 p. 1727). |
| 8. | Arsenic | NMT 2 ppm (as per USP 23, p. 1724). |
| 9. | Residual Solvents | a) Acetone: NMT 0.1% b) Ethanol: NMT 2.0% c) Formaldehyde: NMT 100 ppm |
| 10. | Sodium Hyaluronate Assay | 97.0 to 102.0% (dried basis) |
| 11. | Intrinsic Viscosity | Between 10.0 to 14.5 deciliters per gram. |
| 12. | Molecular Weight (calculated using the Laurent Formula) | Between 500,000 to 800,000 daltons (based on intrinsic viscosity). |
| 13. | Total Aerobic Microbial Count | NMT 50 microorganism/gram (as per USP 23, p. 1684). |
| 14. | Test for Escherichia coli | Escherichia coli is absent (as per USP 23, p. 1685). |
| 15. | Yeasts & Molds | NMT 50 microorganisms/gram (as per USP 23, p. 1686). |
| 16. | Endotoxins (LAL) | NMT 0.07 EU/mg (as per USP 23, p. 1696). |

A topical grade of hyaluronan may, in certain circumstances be suitable and may be made from the following granules/powder which have the following characteristics:

| | Tests | Specifications |
|---|---|---|
| 1. | Description | White or cream-coloured granules or powder, odourless |
| 2. | Identification (IR Spectrum) | Must conform with the Reference Standard Spectrum. |
| 3. | pH (1% Solution) | Between 6.0 and 8.0 at 25 degrees C. |
| 4. | Loss on Drying | NMT 10.0% at 102 degrees C. for 6 hours. |
| 5. | Residue on Ignition | Between 15.0 and 19.0% |
| 6. | Protein Content | NMT 0.40% |
| 7. | Heavy Metals | NMT 20 ppm (as per USP 23 p. 1727). |
| 8. | Arsenic | NMT 2 ppm (as per USP 23, p. 1724). |
| 9. | Residual Solvents | a) Acetone: NMT 0.1% b) Ethanol: NMT 2.0% c) Formaldehyde: NMT 100 ppm |
| 10. | Sodium Hyaluronate Assay | 97.0 to 102.0% (dried basis) |
| 11. | Intrinsic Viscosity | Between 11.5 to 14.5 deciliters per gram. |
| 12. | Molecular Weight (calculated using the Laurent Formula) | Between 600,000 to 800,000 daltons (based on intrinsic viscosity). |
| 13. | Total Aerobic Microbial Count | NMT 100 microorganism/gram (as per USP 23, p. 1684). |
| 14. | Test for Staphylococcus aureus | Staphylococcus aureus is absent (as per USP 23, p. 1684). |
| 15. | Test for Pseudomonas aeruginosa | Pseudomonas aeruginosa is absent (as per USP 23, p. 1684). |
| 16. | Yeasts & Molds | NMT 200 CFU/gram (as per USP 23, p. 1686). |

This topical grade may then be sterilized.

Other forms of hyaluronic acid and/or its salts may be chosen from other suppliers, for example those described in prior art documents disclosing forms of hyaluronic acid having lower molecular weights between about 150,000 daltons and 750,000 daltons being prepared as for example, 1–2% solutions in sterile water for intravenous administration.

The following references teach hyaluronic acid, sources thereof and processes of the manufacture and recovery thereof.

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture Where high molecular weight hyaluronic acid (or salts or other forms thereof) is used, it must, prior to use, be diluted to permit administration and ensure no intramuscular coagulation. Recently, it has been found that large molecular weight hyaluronic acid having a molecular weight exceeding about 1,000,000 daltons self-aggregates and thus, does not interact very well with HA receptors. Thus, the larger molecular weight hyaluronic acid should be avoided.

The invention will now be illustrated by reference to the following Figures and description of embodiments.

DETAILED DESCRIPTION OF EMBODIMENTS

The invention will now be illustrated with reference to the following experimental data and tests performed with respect to embodiments.

The angiostatic steroid tetrahydrocortisol (TH-F), tetrahydrocortisone (TH-E) or tetrahydro-cortexolone (TH-S) and the like s.c at 1 mg/kg of body weight of a mammal is capable of inhibiting angiogenesis in the murine chronic granulomatous air pouch (1). The same effect is obtained with 1 mg/kg s.c cortisone in combination with 1000 U p.o heparin. The cortisone heparin combination also induces regression of the existing neo-vasculature (2). We investigated the use of topical application of angiostatic steroids in combination with hyaluronan (in these examples at a concentration of 2.5% by weight of the composition). Reference is made to article 20 listed previously.

Methods

Chronic granulomatous air pouches were raised in mice by known methods (the reader is referred to PCT/CA94/00207 at page 16 for an experimental method in this regard) utilizing 0.5 ml Freund's Complete adjuvant with 0.1% croton oil injected into 1 day old air pouches. Animals were dosed with saline/0.01% DMSO either subcutaneously (s.c.) into the nape of the neck, or with saline applied topically in 0.1 ml 2.5% hyaluronan. Vascular casts incorporating carmine in gelatin were formed at termination, the tissues weighed dry (mg), papain digested, and the carmine content ($\mu$g) determined by spectrophotometric assay. Vascularity was calculated as the Vascularity Index ($\mu$g/mg). Results are expressed as means±s.e.m.

Results

Investigation of the action of tetrahydrocortisol, tetrahydrocortisone and tetrahydrocortexolone and the like on inflammation-induced angiogenesis in the murine chronic granulomatous air pouch was pursued. Groups of mice (n=8–13) were dosed with tetrahydrocortisol, tetrahydrocortisone or tetrahydrocortexolone or the like (0.1–3.0 mg/kg in 0.1 ml saline/0.01% DMSO, s.c) daily from induction (day 0) to termination on day 6. Controls were dosed with 0.1 ml saline/0.01% DMSO subcutaneously.

TABLE 1

| DRUG | VASCULAR INDEX ($\mu$g/mg) |
| --- | --- |
| Control | 8.31 ± 1.46 |
| Cortisone 1 mg/kg s.c. | 8.23 ± 0.62 |
| Heparin 1000 U p.o. | 7.93 ± 0.83 |
| Heparin & Cortison | 6.03 ± 1.12 |
| TH-F 1 mg/kg s.c. | 5.29 ± 0.61 |
| TH-F & Heparin | 7.11 ± 0.85 |

The angiostatic glucocorticoid cortisone requires simultaneous dosing with heparin (Table 1) to be angiostatic, being inactive when administered alone at the sub-antiinflammatory dose of 1 mg/kg, whereas tetrahydrocortisol etc. may not require heparin. In addition, the co-administration of heparin reduces effectiveness of the tetrahydrosteroid (Table 1).

Table 2

Investigation of the action of angiostatic and anti-inflammatory steroids on inflammation-induced angiogenesis in the murine chronic granulomatous air pouch was pursued. Groups of mice (n=8–13) were treated with the steroids at 1.0 mg/kg (0.1 ml saline/0.01% DMSO, s.c), except of dexamethasone at (0.2 mg/kg), daily from the day of induction (day 0) to termination on day 6. Controls were given 0.1 ml saline/0.01% DMSO s.c. (Key: Tetrahydrocortisol (TH-F), Tetrahydrocortisone (TH-E).

| Treatment | Vascular Index $\mu$g/mg |
| --- | --- |
| Saline/DMSO | 15.774 ± 1.152 |
| TH-F | 13.088 ± 1.630 |
| TH-E | 18.860 ± 1.830 |

Table 3

Investigation of the action of tetrahydrocortisol, tetrahydrocortisone and tetrahydrocortexolone and the like on the established 7-day old vasculature of the murine chronic granulomatous air pouch was pursued. Groups of mice were dosed with tetrahydrocortisol, tetrahydrocortisone or tetrahydrocortexolone or the like (0.1–3.0 mg/kg in 0.1 ml saline/0.01% DMSO, s.c) daily from day 7 to termination at day 14 or day 21. Controls were dosed with 0.1 ml saline (0.01% DMSO alone).

| Day/Treatment | Vascular Index $\mu$g/mg |
| --- | --- |
| Day 7 Saline | 10.638 ± 0.883 |
| Day 14 Saline | 17.97 ± 2.10 |
| 0.1 TH-E | 18.18 ± 1.97 |
| 0.3 TH-E | 20.38 ± 1.91 |
| 1.0 TH-E | 22.49 ± 3.77 |
| 3.0 TH-E | 18.87 ± 1.29 |
| Day 21 Saline | 29.98 ± 2.66 |
| 0.1 TH-E | 18.59 ± 1.84 |
| 0.3 TH-E | 31.33 ± 2.91 |
| 1.0 TH-E | 25.75 ± 2.40 |
| 3.0 TH-E | 25.91 ± 1.85 |

Table 4

Investigation of the action of topical tetrahydrocortisol, tetrahydrocortisone, tetrahydrocortexolone and the like on inflammatory-induced angiogenesis in the murine chronic granulomatous air pouch was pursued. Groups of mice (n=8–13) were depilated and the inflammation induced 4 days later. Tetrahydrocortisol (TH-F) and tetrahydrocortisone (TH-E) were applied topically (1 mg/kg) in 2.5% hyaluronan (0.1 ml) daily from the day of induction (day 0) to termination (day 6). Controls were dosed with 0.1 ml 2.5% hyaluronan alone.

| Treatment | Vascular Index µg/mg |
|---|---|
| HA Control | 11.180 ± 1.980 |
| HA + TH-E | 21.118 ± 1.927 |
| HA + TH-F | 29.394 ± 2.213 |

Table 5

Investigation of the action of topical tetrahydrocortisol, tetrahydrocortisone and tetrahydrocortexolone and the like on inflammatory-induced angiogenesis in the murine chronic granulomatous air pouch was pursued. Groups of mice (n=8–13) were depilated and the inflammation induced 4 days later. Tetrahydrocortisol (TH-F) was applied topically with 2.5% hyaluronan (0.1 ml of composition 0.1–1.0 mg of tetrahydrocortisol/kg) by weight daily from the day of induction (day 0) to termination (day 6). Controls were dosed with 0.1 ml 2.5% hyaluronan alone.

| Treatment | Vascular Index µg/mg |
|---|---|
| HA | 11.180 ± 1.98 |
| HA + TH-F | 11.800 ± 1.920 |
| HA + TH-F | 12.250 ± 0.230 |
| HA + TH-F | 15.73 ± 3.218 |

Conclusions

The data supports the conclusion that the angiostatic action of tetrahydrocortisol, tetrahydrocortisone and tetrahydrocortexolone and the like on subcutaneous administration in the absence of heparin is unique amongst the angiostatic steroids. The angiostatic glucocorticoid cortisone requires simultaneous dosing with heparin (Table 1) to be angiostatic, being inactive when administered alone at the sub-antiinflammatory dose of 1 mg/kg, whereas tetrahydrocortisol etc. may not require heparin. In addition, the co-administration of heparin reduces effectiveness of the tetrahydrosteroid (Table 1). Another tetrahydrosteroid (TH-E) was without effect in the absence of heparin whether dosed prophylactically (Table 2) or therapeutically (Table 3). In this instance, tetrahydrocortisol, tetrahydrocortisone and tetrahydrocortexolone and the like induced a decrease in vascularity (Table 1).

Contrary to this, the topical application of tetrahydrocortisol, tetrahydrocortisone and tetrahydrocortexolone and the like in 2.5% hyaluronan resulted in significant acceleration of angiogenesis (Table 4), which in the case of tetrahydrocortisol, tetrahydrocortisone and tetrahydrocortexolone and the like, was dose related. The application of angiostatic steroids with hyaluronan resulted in a potentiation of the ability of tetrahydrocortisol, tetrahydrocortisone and tetrahydrocortexolone and the like to raise vascularity, whilst the angiostatic action of tetrahydrocortisol, tetrahydrocortisone and tetrahydrocortexolone and the like was converted into profound stimulation of angiogenesis (compare Tables 2, 4 & 5). We have previously investigated that the angiostatic glucocorticoid cortisone, given topically at 1 mg/kg of body weight, is angiostatic in combination with 2.5% hyaluronan. There may therefore be a structural basis to the diverse pharmacological actions noted with this steroid series, in their interaction with hyaluronan. The 3-ketone combination with A4 double bond may result in an angiostatic profile in conjunction with hyaluronan. These groups are required for glucocorticoid activity, their reduction leading to the absence of glucocorticoid activity in the tetrahydro-derivatives and stimulation of angiogenesis in the presence of HA.

It should be noted that proprietary formulations of topical hydrocortisone are typically 0.1–1.0% whilst the formulations used in these studies contain a maximum of 0.02% angiostatic steroid in 2.5% hyaluronan.

From these studies, topical applications of tetrahydro-derivatives of corticosteroids devoid of glucocorticoid activity in hyaluronan would be beneficial for the acceleration of wound healing via the stimulation of angiogenesis. Inherent in this observation is that they could be contra-indicated for conditions dependent on neovascularisation, such as superficial carcinomas. The reader is referred to, the British Journal of Pharm. 107:259P,1992, 1st International Workshop Hyaluronan Delivery, Royal Soc. Med. Round Table series 33:21–31, 1994 and 2nd International Workshop Hyaluronan Delivery, Royal Soc. Med. Round Table series 1995.

The following represents typical chemical structures of basic angiostatic steroids which may be utilized in combination with hyaluronic acid to induce angiogenesis and foster wound healing. The list is not considered to be exhaustive but are believed merely representative.

| | |
|---|---|
| tetrahydrocortisol | 5-pregnane-3,11,17,21-tetrol-20-one |
| tetrahydrocortisone | 5-pregnane-3,17,21-triol-11,20-dione |
| 17-hydroxyprogesterone | 4-pregnene-17-ol-3,20-dione |
| medroxyprogesterone | 6-methyl-5-pregnene-17-ol-3,20-dione |
| 6,6'-dehydromedroxyprogesterone | 6-methylene-5-pregnene-17-ol-3,20-dione |
| megestrol | 17-hydroxy-6-methyl-4,6-pregnadiene-3,20-dione |
| 1-dehydro-megestrol | 17-hydroxy-6-methyl-1,4,6-pregnatriene-3,20-dione |
| melengestrol | 17-methylene-6-methyl-4,6-pregnadiene-3,20-dione |
| 1-dehydro-melengestrol | 17-methylene-6-methyl-1,4,6-pregnatriene-3,20-dione |
| 2-methoxyoestradiol | 1,3,5(10)-oestratriene-2,3,17-triol-2-methyl ether |
| 2-hydroxyoestrone | 1,3,5(10)-oestratriene-2,3-diol-17-one |
| 4-methoxyoestradiol | 1,3,5(10)-oestratriene-3,4,17-triol-4-methyl ether |
| 2-methoxyoestradiol 3-methyl ether | 1,3,5(10)-oestratriene-2,3,17-triol-2,3-dimethyl ether |
| 2-methoxyoestrone | 1,3,5(10)-oestratriene-2,3-diol-17-one-2-methyl ether |
| 2-hydroxyoestradiol | 1,3,5(10)-oestratriene-2,3,17-triol |
| 2-methoxyoestriol | 1,3,5(10)-oestratriene-2,3,16,17-tetrol-2-methyl ether |
| 2-hydroxyoestradiol 3-methyl ether | 1,3,5(10)-oestratriene-2,3,17-triol-3-methyl ether |

Definite angiogenesis action was obtained utilizing tetrahydrocortisol where $R_1$=—OH and tetrahydrocortisone where $R_1$==O The following chart indicates the various predictable forms that steroids should take:

| | $R_1$ | $R_2$ | $R_3$ | $R_4$ | $R_5$ | $R_6$ |
|---|---|---|---|---|---|---|
| Tetrahydrocortexolone | —OH | —H | —H | —H | —OH | —OH |
| 17 Hydroxyprogester-one | =O | = | —H | —OH | —H | |

Further positive results are also predicted for acetate derivatives

The following chart indicates further acetate derivatives which may be effective:

-continued

| | $R_1$ | $R_2$ | $R_3$ |
|---|---|---|---|

The following chart indicates further various predictable forms for applicable steroids:

| | $R_1$ | $R_2$ | $R_3$ | $R_4$ | $R_5$ | $R_6$ | $R_7$ |
|---|---|---|---|---|---|---|---|
| Medroxyprogesterone | —H | —H | = | | —CH$_3$ | —H | —H |
| 6:6'-dehydro-medroxyprogesterone | —H | —H | = | | =CH$_2$ | —H | —H |
| Megestrol | —H | —H | = | | \|=<br>CH$_3$ | | —H |
| 1-dehydro-medroxyprogesterone | = | = | | | \|=<br>CH$_3$ | | —H |
| Melengestrol | —H | —H | = | | \|=<br>CH$_3$ | | =CH$_2$ |
| 1-dehydro melengestrol | = | = | | | \|=<br>CH$_3$ | | =CH$_2$ | and also 17-OH or 17-H or the following derivatives:

All steroids conjugated at the 20 position ($R_1$) were applicable (i.e. not the oestrogens)

or

All steroids conjugated at the 3 position ($R_1$) with heparin adipic hydrazide or heparin hydrazide

The following chart indicates further various other acceptable steroids utilized:

|  | R1 | R2 | R3 | R4 | R5 |
|---|---|---|---|---|---|
| 2-methoxyestradiol | —OCH$_3$ | —OH | —H | —OH | —H |
| 2-hydroxyestrone | —OH | —OH | —H | =O | —H |
| 4-methoxyestradiol | —H | —OH | —OCH$_3$ | —OH | —H |
| 2-methoxyestradiol 3-methyl ether | —OCH$_3$ | —OCH$_3$ | —H | —OH | —H |
| 2-methoxyestrone | —OCH$_3$ | —OH | —H | —OH | —H |
| 2-hydroxyestradiol | —OH | —OH | —H | —OH | —H |
| 2-methoxyestriol | —OCH$_3$ | —OH | —H | —OH | —OH |
| 2 Hydroxyestradiol 3-methyl ether | —OH | —OCH$_3$ | —H | —OH | —H |

Known Structure of angiostatic steroids.

TETRAHYDROCORTISOL
(5β-pregnane-3α, 11β, 17α, 21-tetrol-20-one; Tetrahydro-F)

TETRAHYDROCORTISONE
(5β-pregnane-3α, 17α, 21-triol-11, 20-dione; Tetrahydro-E)

-continued
TETRAHYDROXYCORTEXOLONE
(5β-pregnane-3α, 17α, 21-triol-20-one; Tetrahydro-S; 11-deoxytetrahydrocortisol)

Figure 1:
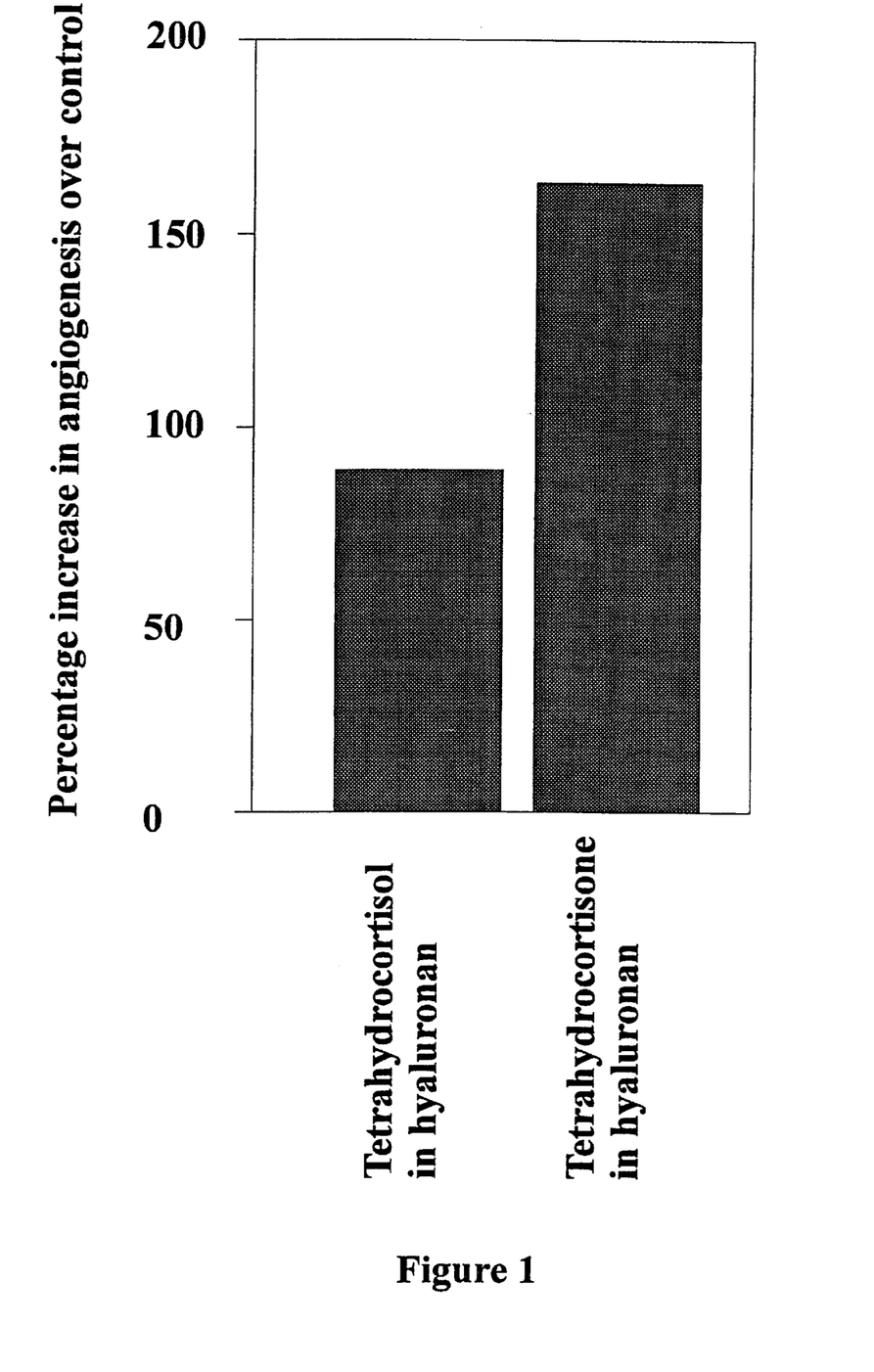
FIG. 1 is a graph showing the effect of two angiostatic steroids applied topically in hyaluronan to mice with granulomatous air pouches against a control.

Referring now to FIG. 1, it may be observed that firstly different angiostatic steroids have varying effects in terms of their percentage increase in angiogenesis over a control. Significant, however, is the fact that all angiostatic steroids tested provided a marked increase in angiogenesis over either the control, the angiostatic steroid alone, or HA alone. This is verified when reviewing the tables described above.

Figure 2:
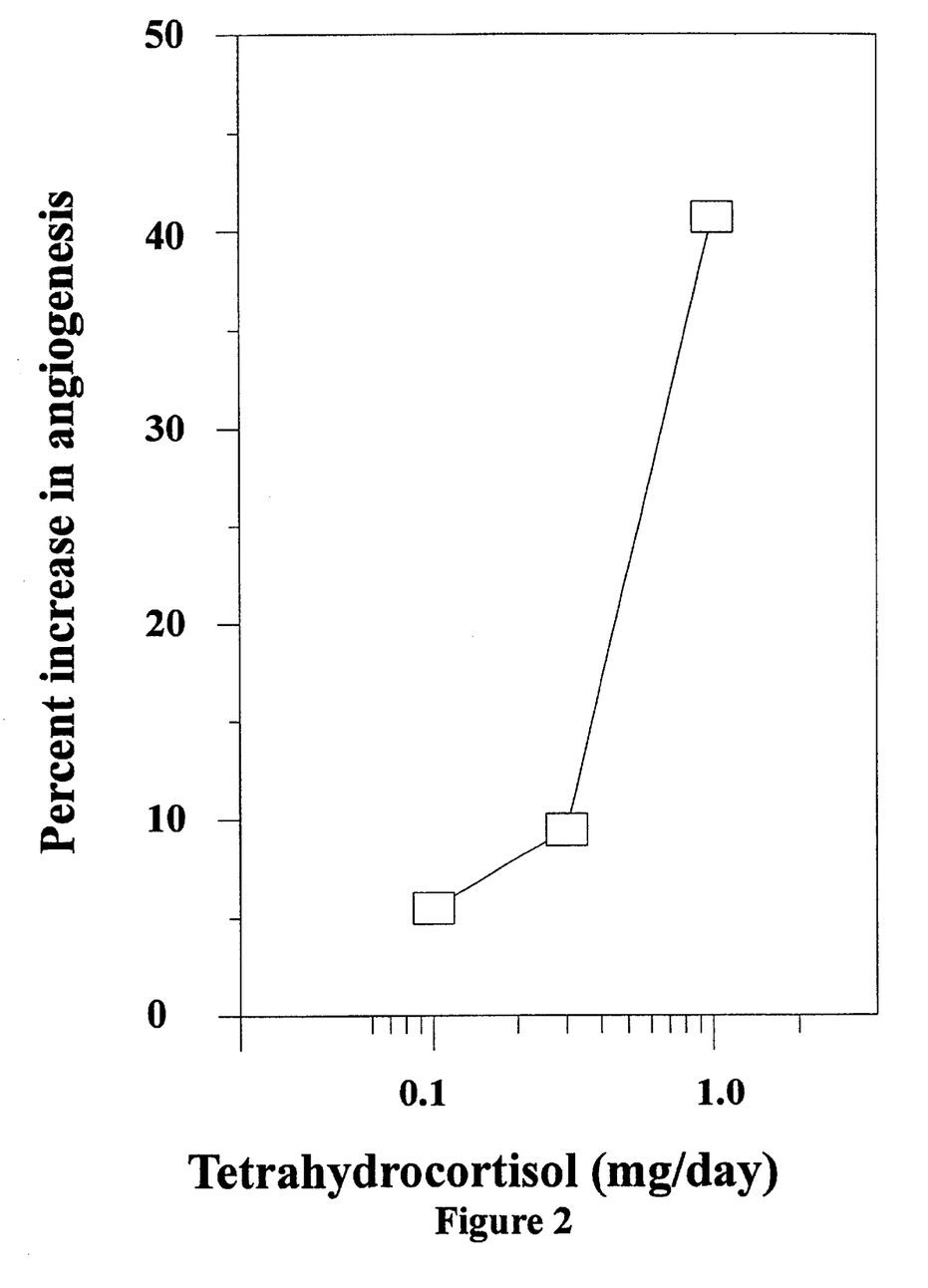
FIG. 2 is a graph showing the increase of angiogenesis over a control of varying concentrations of topical tetrahydrocortisol applied daily in hyaluronan to murine granulomatous tissue.

Referring now to FIG. 2, it may be seen for tetrahydrocortisol, and it is expected for the other angiostatic steroids listed above as well, that within the range of 0.1–1 mg of the angiostatic steroid administered/day, which is significantly less than the amount of steroid used for wound healing when utilizing glucocorticoid or mineralocorticoid steroids such as cortisone, which is up to 3 mg/day when utilized alone, that a significant increase in neovascularization can be produced in utilizing the combination of hyaluronan (HA) plus an angiostatic steroid in substantially reduced amounts to limit the impact of the consumption of steroids on the individual, and yet realize the objectives of fostering angiogenesis and accelerating wound healing.

Figure 3:
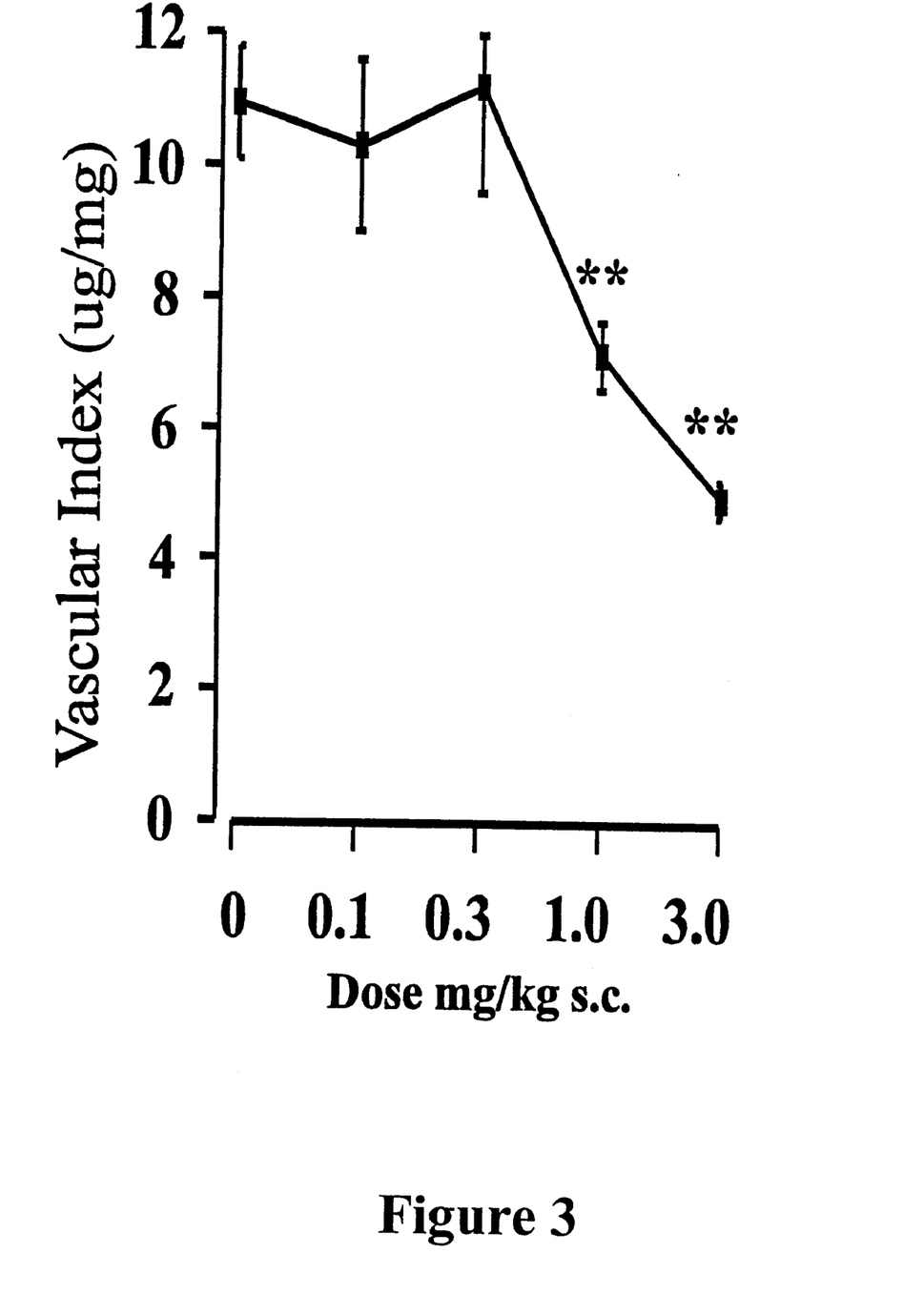
FIG. 3 is a graph illustrating typical activity of an angiostatic steroid alone and the predictable decrease in angiogenesis as the dose of this steroid is increased.

FIG. 3 illustrates typical activity of an angiostatic steroid alone with the predictable decrease in angiogenesis as the dose is increased.

All of the aforementioned data supports the conclusion of HA and steroids of the type listed above, in combination, acting synergistically to induce angiogenesis in wound healing for example leg ulcers and pressure ulcers developed during various stages of diabetes. Also, the trend is such that the form of HA and the angiostatic steroid taken from the listed alternatives above induces angiogenesis much more than HA alone, or for that matter any of the listed angiostatic steroids alone. The results of the tests and experiments firmly establish that forms of hyaluronic acid (for example sodium hyaluronate having a molecular weight less than 750,000 daltons–e.g. 225,000 daltons) in combination with known angiostatic steroids act to induce angiogenesis and neovascularization in wound healing without the known systemic side effects of angiogenic glucocorticoid or mineralocorticoid steroids.

It will also be appreciated by those skilled in the art that the processes, uses, compositions and dosage forms according to aspects of the invention may be applied to induce angiogenesis in other instances where angiogenesis is desired. It is therefore clear that many uses can be made of embodiments and aspects of this invention without departing from the scope thereof. It is therefore intended that all material contained herein be interpreted as illustrative of the invention and not in a limiting sense.

The embodiments of the invention in which an exclusive property or privilege is claimed are as follows:

1. A pharmaceutical composition for increasing neovascularization and angiogenesis during wound healing in a mammal beyond the level of neovascularization and angiogenesis which would occur at the wound site without any treatment, said composition comprising an effective amount of an angiostatic steroid combined with an effective amount of hyaluronic acid or a pharmaceutically acceptable salt thereof having a molecular weight less than about 750,000 daltons, to promote neovascularization and angiogenesis, wherein said angiostatic steroid is not a glucocorticoid, mineralcorticoid, or sex steroid.

2. The composition of claim 1 wherein said composition also includes a suitable diluent.

3. The composition of claim 1 wherein said composition is in a form suitable to be administered nasally, vaginally, intraaurally, ocularly, rectally, orally, locally or topically, intramuscularly, intermuscularly, transdermally or intravenously.

4. The composition of claim 3 wherein the amounts of the steroid is selected from between about 0.1–3 mg of the steroid per kg of body weight and the amount of hyaluronan is between about 0.1–20% by weight of the composition.

5. The composition of claim 4 wherein hyaluronan is 2.5% by weight of the composition.

6. A method of treatment for increasing neovascularization and angiogenesis during wound healing in a mammal beyond the level of neovascularization and angiogenesis which would occur at the wound site without any treatment, said method comprising application of a composition comprising an effective amount of an angiostatic steroid combined with an effective amount of a form of hyaluronic acid and/or pharmaceutically acceptable salts thereof at the wound site, said application of the combination being for such period as required wherein the molecular weight of the form of hyaluronic acid has a molecular weight less than about 750,000 daltons and said angiostatic steroid is not a glucocorticoid, mineralcorticoid, or sex steroid.

7. The method of claim 6 wherein said composition also includes a suitable diluent.

8. The method of claim 6 wherein the composition is applied or administered nasally, rectally, vaginally, intraaurally, ocularly, orally, locally, topically, intramuscularly, intermuscularly, transdermally or intravenously.

9. The method of claim 8 wherein the amounts of the steroid is selected from between about 0.1–3 mg of the steroid per kg of body weight and the amount of hyaluronan is between about 0.1–20% by weight of the composition.

10. The method of claim 9 wherein hyaluronan is 2.5% by weight of the composition.

11. A composition for inducing angiogenesis in the healing of a condition, said composition comprising hyaluronic acid in a suitable form in combination with a suitable steroid, which is not a glucocorticoid, mineralcorticoid, or sex steroid, said suitable steroid being known not to stimulate new blood vessel formation when utilized individually, wherein the combination of hyaluronic acid and said suitable steroid stimulates new blood vessel formation and angiogenesis to accelerate scarless healing of a condition, the molecular weight of the form of hyaluronic acid being less than about 750,000 daltons.

12. The composition of claim 11 wherein said suitable steroids are angiostatic steroids.

13. The composition of claim 12 wherein said angiostatic steroids are tetrahydro-steroids.

14. The composition of claim 11, 12, or 13 wherein the condition being treated is a wound.

15. The composition of claim 12 wherein said suitable angiostatic steroid is selected from the group consisting of tetrahydrocortisol (TH-F), tetrahydrocortisone (TH-E), tetrahydrocortexolone (TH-S) and combinations thereof.

16. The combination of an effective amount of a form of hyaluronic acid selected from the group consisting of hyaluronic acid and pharmaceutically acceptable salts thereof with a tetrahydro-steroid derivative utilized for acceleration of wound healing by the stimulation of angiogenesis.

17. A process for the stimulation and/or induction of angiogenesis in a mammal, the process comprising the steps of administering at least one effective dosage amount of a pharmaceutical composition for the stimulation and/or induction of angiogenesis to a site on/in a mammal in need of stimulation and/or induction of angiogenesis for the time as required, each effective dosage amount of the composition comprising an effective non-toxic dosage amount of the composition comprising an effective non-toxic dosage amount of a steroid known to have angiostatic properties when utilized alone or in combination with known therapies and a non-toxic effective dosage amount of hyaluronic acid and/or a pharmaceutically acceptable salt thereof having a molecular weight less than about 750,000 daltons, wherein said steroid is not a glucocorticoid, mineralcorticoid, or sex steroid.

18. The process of claim 17 utilized for stimulation of blood vessel growth in a wound.

19. The process of claim 17 wherein said steroid known to have angiostatic properties is a tetrahydro-steroid.

20. The process of claim 17 wherein said steroid known to have angiostatic properties is selected from the group consisting of tetrahydrocortisone, tetrahydrocortisol and tetrahydrocortexolone.

21. The process of claim 17 wherein said hyaluronic acid or pharmaceutically acceptable salt thereof is sodium hyaluronate.

22. The composition of claim 1 wherein the composition is in a form to be administered topically in the form of a cream, lotion and/or gel for the treatment of burns, ulcers or incisions, nasally, vaginally, intraaurally, ocularly or orally for the treatment of wounds therein or as a suppository for hemorrhoids.

23. The method of claim 6 wherein the composition is administered in a form topically as a cream, lotion and/or gel for the treatment of burns, ulcers, or incisions, nasally, vaginally, intraaurally, ocularly or orally for the treatment of wounds therein or as a suppository for hemmorhoids.

24. The composition of claim 11 wherein the composition is administered in a form topically as a cream, lotion and/or gel for the treatment of burns, ulcers, or incisions, nasally, vaginally, intraaurally, ocularly or orally for the treatment of wounds therein or as a suppository for hemmorhoids.

25. The process of claim 17 wherein the composition is administered in a form topically as a cream, lotion and/or gel for the treatment of burns, ulcers or incisions, nasally, vaginally, intraaurally, ocularly or orally for the treatment of wounds therein or as a suppository for hemorrhoids.

26. An effective non-toxic dosage amount of a composition comprising an effective non-toxic dosage amount of sodium hyaluronate having a molecular weight less than about 750,000 daltons and a therapeutically effective non-toxic dosage amount of a known angiostatic steroid used to stimulate and induce angiogenesis, wherein said angiostatic steroid is not a glucocorticoid, mineralcorticoid, or sex steroid.

27. The dosage amount of claim 26 wherein said angiostatic steroid is selected from tetrahydro-steroids.

28. The dosage of claim 26 wherein the amount of angiostatic steroid is selected from between about 0.1–3 mg of the steroid per kg of body weight and the amount of hyaluronan is between about 0.1–20% by weight of the composition for wounds in the order of 4 sq. cm.

29. A pharmaceutical composition effective for the stimulation and induction of angiogenesis, the pharmaceutical composition containing a plurality of dosage amounts for stimulating and inducing angiogenesis, each of said dosage amounts comprising a therapeutically effective non-toxic (to the patient) dosage amount of a steroid known to be angiostatic, and an effective non-toxic dosage amount of the hyaluronic acid and/or pharmaceutically acceptable salts thereof to stimulate and induce angiogenesis, the molecular weight of the form of hyaluronic acid being less than about 750,000 daltons, wherein said steroid is not a glucocorticoid, mineralcorticoid, or sex steroid.

30. The composition of claim 1, 11, or 29 further comprising suitable excipients depending upon the route of administration to make a gel, lotion, spray, ointment, suppository, or cream.

31. The method of claim 6 wherein said composition further comprises suitable excipients depending upon the route of administration to make a gel, lotion, spray, ointment, suppository, or cream.

32. The process of claim 17 wherein said composition further comprises suitable excipients depending upon the route of administration to make a gel, lotion, spray, ointment, suppository, or cream.

33. The dosage of claim 26 wherein said composition further comprises suitable excipients depending upon the route of administration to make a gel, lotion, spray, ointment, suppository, or cream.

34. A dosage amount of a pharmaceutical composition for stimulating and inducing angiogenesis at a wound site, the composition comprising:

(1) a known angiostatic steroid agent, which is not a glucocorticoid, mineralcorticoid, or sex steroid; and (2) hyaluronic acid and/or pharmaceutically acceptable salts thereof having a molecular weight less than about 750,000 daltons characterized in that said composition:

(a) is in a dosage form which is suitable for administration at the wound site; and (b) is in such an amount and in such form that each of component (1) and (2) are in an effective dosage amount together to stimulate and induce angiogenesis.

35. The dosage form of claim 34 wherein the pharmaceutical composition may further comprise a plurality of dosage amounts.

36. A method of treatment comprising administering to a host in need thereof a form of hyaluronic acid having a molecular weight less than about 750,000 daltons with suitable angiostatic steroids, which are not glucocorticoids, mineralocorticoids or sex steroids.

37. A pharmaceutical composition comprising a form of hyaluronic acid having a molecular weight less than about 750,000 daltons with suitable angiostatic steroids, which are not glucocorticoids, mineralocorticoids or sex steroids.

38. A dosage amount of a composition comprising a form of hyaluronic acid having a molecular weight less than about 750,000 daltons with suitable angiostatic steroids, which are not glucocorticoids, mineralocorticoids or sex steroids.

* * * * *